US009113907B2

(12) United States Patent
Allen, IV et al.

(10) Patent No.: US 9,113,907 B2
(45) Date of Patent: Aug. 25, 2015

(54) VESSEL SEALING INSTRUMENT WITH CUTTING MECHANISM

(71) Applicant: COVIDIEN LP, Mansfield, MA (US)

(72) Inventors: James D. Allen, IV, Broomfield, CO (US); James S. Cunningham, Boulder, CO (US); Victor K. Appel, Longmont, CO (US); Glenn A. Horner, Boulder, CO (US)

(73) Assignee: Covidien LP, Mansfield, MA (US)

( * ) Notice: Subject to any disclaimer, the term of this patent is extended or adjusted under 35 U.S.C. 154(b) by 113 days.

(21) Appl. No.: 14/086,399

(22) Filed: Nov. 21, 2013

(65) Prior Publication Data

US 2014/0081265 A1  Mar. 20, 2014

Related U.S. Application Data

(60) Continuation of application No. 13/227,220, filed on Sep. 7, 2011, now Pat. No. 8,591,510, which is a division of application No. 12/233,157, filed on Sep. 18, 2008, now abandoned.

(51) Int. Cl.
*A61B 18/04* (2006.01)
*A61B 18/18* (2006.01)
(Continued)

(52) U.S. Cl.
CPC ........... *A61B 18/1445* (2013.01); *A61B 17/282* (2013.01); *A61B 17/285* (2013.01); *A61B 17/2816* (2013.01); *A61B 17/3203* (2013.01); *A61B 2018/00345* (2013.01); *A61B 2018/00404* (2013.01); *A61B 2018/00601* (2013.01);
(Continued)

(58) Field of Classification Search
CPC ........... A61B 18/1445; A61B 17/2816; A61B 17/282; A61B 2018/00404; A61B 2018/00601; A61B 2018/1455
See application file for complete search history.

(56) References Cited

U.S. PATENT DOCUMENTS

D249,549 S    9/1978  Pike
D263,020 S    2/1982  Rau, III
(Continued)

FOREIGN PATENT DOCUMENTS

CN    201299462          9/2009
DE    2415263 A1         10/1975
(Continued)

OTHER PUBLICATIONS

US. Appl. No. 08/926,869, filed Sep. 10, 1997, James G. Chandler.
(Continued)

*Primary Examiner* — Rebecca E Eisenberg

(57) ABSTRACT

An end effector assembly for use with an instrument for sealing and cutting tissue includes a pair of opposing first and second jaw members movable relative to the to grasp tissue therebetween. Each jaw member including a jaw housing and an electrically conductive surface adapted to connect to a source of electrosurgical energy such that the electrically conductive surfaces are capable of conducting electrosurgical energy through tissue held therebetween to effect a tissue seal. One of the electrically conductive surfaces including a channel defined therein and extending along a length thereof that communicates with a nozzle disposed in the jaw housing. The nozzle is configured to direct high pressure fluid from a fluid source into the channel for cutting tissue grasped between the jaw members.

12 Claims, 6 Drawing Sheets

(51) Int. Cl.
*A61B 18/14* (2006.01)
*A61B 17/28* (2006.01)
*A61B 17/285* (2006.01)
*A61B 17/3203* (2006.01)
*A61B 18/00* (2006.01)

(52) U.S. Cl.
CPC ............... *A61B2018/00619* (2013.01); *A61B 2018/1412* (2013.01); *A61B 2018/1455* (2013.01)

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinge |
| D541,938 S | 5/2007 | Kerr et al |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 8,591,510 B2 | 11/2013 | Allen, IV et al. |
| 2003/0236518 A1 | 12/2003 | Marchitto et al. |
| 2004/0199226 A1 | 10/2004 | Shadduck |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 10045375 C2 | 10/2002 |
| DE | 202007009165 U1 | 8/2007 |
| DE | 202007009317 U1 | 8/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1 159 926 A2 | 12/2001 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-317934 A | 12/1996 |
| JP | 9-10223 C | 1/1997 |
| JP | 9-122138 A | 5/1997 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000342599 A | 12/2000 |
| JP | 2000350732 A | 12/2000 |
| JP | 2001-8944 | 1/2001 |
| JP | 2001-29356 | 2/2001 |
| JP | 2001128990 A | 5/2001 |
| JP | 2001-190564 A | 7/2001 |
| JP | 2004-517668 A | 6/2004 |
| JP | 2004-528869 A | 9/2004 |
| SU | 401367 A1 | 10/1973 |
| WO | 0036986 A1 | 6/2000 |
| WO | 0115614 A1 | 3/2001 |
| WO | 0154604 A1 | 8/2001 |
| WO | 2005/110264 A2 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010, Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Horner.
U.S. Appl. No. 12/769,444, filed Apr. 28, 2010, Glenn A. Norner.
U.S. Appl. No. 12/770,369, filed Apr. 29, 2010, Glenn A. Horner.
U.S. Appl. No. 12/770,380, filed Apr. 29, 2010, Glenn A. Horner.

(56) References Cited

OTHER PUBLICATIONS

U.S. Appl. No. 12/770,387, filed Apr. 29, 2010, Glenn A. Horner.
U.S. Appl. No. 12/773,526, filed May 4, 2010, Duane E. Kerr.
U.S. Appl. No. 12/773,644, filed May 4, 2010, Thomas J. Gerhardt.
U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Horner.
U.S. Appl. No. 12/792,051, filed Jun. 2, 2010, David M. Garrison.
U.S. Appl. No. 12/792,068, filed Jun. 2, 2010, Glenn A. Horner.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.
U.S. Appl. No. 12/843,384, filed Jul. 26, 2010, David M. Garrison.
U.S. Appl. No. 12/845,203, filed Jul. 28, 2010, Gary M. Couture.
U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. 12/861,198, filed Aug. 23, 2010, James A. Gilbert.
U.S. Appl. No. 12/861,209, filed Aug. 23, 2010, William H. Nau, Jr.
U.S. Appl. No. 12/876,668, filed Sep. 7, 2010, Sara E. Anderson.
U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,731, filed Sep. 7, 2010, Kristin D. Johnson.
U.S. Appl. No. 12/877,199, filed Sep. 8, 2010, Arlen J. Reschke.
U.S. Appl. No. 12/877,482, filed Sep. 8, 2010, Gary M. Couture.
U.S. Appl. No. 12/895,020, filed Sep. 30, 2010, Jeffrey M. Roy.
U.S. Appl. No. 12/896,100, filed Oct. 1, 2010, Ryan Artale.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/029,390, filed Feb. 17, 2011, Michael C. Moses.
U.S. Appl. No. 13/030,231, filed Feb. 18, 2011, Jeffrey M. Roy.
U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/075,847, filed Mar. 30, 2011, Gary M. Couture.
U.S. Appl. No. 13/080,383, filed Apr. 5, 2011, David M. Garrison.
U.S. Appl. No. 13/083,962, filed Apr. 11, 2011, Michael C. Moses.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.

(56) References Cited

OTHER PUBLICATIONS

U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.

Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.

(56) References Cited

OTHER PUBLICATIONS

Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 185386.9 dated Jan. 10, 2011.
Int'l Search Report EP 10 185405.7 dated Jan. 5, 2011.
Int'l Search Report EP 09 004476.8 dated Sep. 9, 2009.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10.169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182022.3 dated Mar. 11, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 161117.4 dated Jun. 30, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.

VESSEL SEALING INSTRUMENT WITH CUTTING MECHANISM

CROSS-REFERENCE TO RELATED APPLICATIONS

The present application is a continuation application of U.S. patent application Ser. No. 13/227,220 filed on Sep. 7, 2011, which is a divisional application of U.S. patent application Ser. No. 12/233,157 filed on Sep. 18, 2008, now abandoned, the disclosures of all of which are herein incorporated by reference in their entireties.

BACKGROUND

The present disclosure relates to a forceps used for both endoscopic and open surgical procedures that includes a variety of electrode assemblies configured to allows a user to selectively treat and/or cut tissue. More particularly, the present disclosure relates to a forceps that includes a pair of opposing jaw members configured to grasp tissue and allow a user to selectively treat tissue utilizing electrosurgical energy and/or allow a user cut tissue utilizing one or more mechanical or electro-mechanical cutting mechanisms.

TECHNICAL FIELD

Open or endoscopic electrosurgical forceps utilize both mechanical clamping action and electrical energy to effect hemostasis. The electrode of each opposing jaw member is charged to a different electric potential such that when the jaw members grasp tissue, electrical energy can be selectively transferred through the tissue. A surgeon can either cauterize, coagulate/desiccate and/or simply reduce or slow bleeding, by controlling the intensity, frequency and duration of the electrosurgical energy applied between the electrodes and through the tissue. In order to effectively seal vessels or tissue, two predominant mechanical parameters must be accurately controlled: the pressure applied to the tissue; and the gap distance between the electrodes.

Vessel or tissue sealing is more than "cauterization" which involves the use of heat to destroy tissue (also called "diathermy" or "electrodiathermy"). Vessel sealing is also more than "coagulation" which is the process of desiccating tissue wherein the tissue cells are ruptured and dried. "Vessel sealing" is defined as the process of liquefying the collagen, elastin and ground substances in the tissue so that the tissue reforms into a fused mass with significantly-reduced demarcation between the opposing tissue structures.

Typically and particularly with respect to endoscopic electrosurgical procedures, once a vessel is sealed, the surgeon has to remove the sealing instrument from the operative site, substitute a new instrument through the cannula and accurately sever the vessel along the newly formed tissue seal. As can be appreciated, this additional step may be both time consuming (particularly when sealing a significant number of vessels) and may contribute to imprecise separation of the tissue along the sealing line due to the misalignment or misplacement of the severing instrument along the center of the tissue seal.

SUMMARY

The present disclosure relates to an end effector assembly for use with an instrument for sealing and cutting tissue and includes a pair of opposing first and second jaw members movable relative to the other from a first position wherein the jaw members are disposed in spaced relation relative to one another to a second position wherein the jaw members cooperate to grasp tissue therebetween. Each jaw member includes a jaw housing and an electrically conductive surface adapted to connect to a source of electrosurgical energy such that the electrically conductive surfaces are capable of conducting electrosurgical energy through tissue held therebetween to effect a tissue seal. One (or both) of the electrically conductive surfaces includes a channel defined therein that extends along a length thereof that communicates with a nozzle disposed in the jaw housing. The nozzle is configured to direct high pressure fluid from a fluid source into the channel for cutting tissue grasped between the jaw members.

In one embodiment, the nozzle communicates with one or more fluid conduits disposed within the jaw housing that are configured to convey high pressure fluid from a fluid source. One or more valves may be included that are configured to regulate the flow of high pressure fluid from the fluid source.

In another embodiment, each electrically conductive surface includes a channel defined therein that extends along a length thereof that communicates with a corresponding nozzle disposed within each respective jaw housing. The nozzle(s) may be tapered either longitudinally or transversally depending upon a particular purpose.

The present disclosure also relates to an end effector assembly for use with an instrument for sealing and cutting tissue and includes a pair of opposing first and second jaw members movable relative to the other from a first position wherein the jaw members are disposed in spaced relation relative to one another to a second position wherein the jaw members cooperate to grasp tissue therebetween. Each jaw member includes a jaw housing and an electrically conductive surface adapted to connect to a source of electrosurgical energy such that the electrically conductive surfaces are capable of conducting electrosurgical energy through tissue held therebetween to effect a tissue seal. An adhesive strip is disposed along a length of one (or both) of the electrically conductive surfaces. After electrical activation of the electrically conductive surfaces to effect a tissue seal, the adhesive strip is configured to retain a portion of the tissue seal to essentially tear the portion of the tissue seal away from remaining tissue when the tissue is removed from between the jaw members. The adhesive strip may be configured to include a heat-activated adhesive.

In one embodiment, the adhesive strip includes a plurality of nozzles disposed in the jaw housing operatively coupled to an adhesive fluid supply. The plurality of nozzles may be configured to communicate with one or more fluid conduits disposed within the jaw housing that convey the adhesive fluid from an adhesive fluid supply. One or more valves may be included that are configured to regulate the flow of adhesive fluid from the adhesive fluid supply. One or more of the plurality of nozzles may be tapered to direct the flow of the adhesive fluid onto the adhesive strip in a uniform and consistent manner to facilitate separation of tissue. The adhesive fluid supply may include a heat-activated adhesive fluid.

The present disclosure also relates to an end effector assembly for use with an instrument for sealing and cutting tissue and includes a pair of opposing first and second jaw members movable relative to the other from a first position wherein the jaw members are disposed in spaced relation relative to one another to a second position wherein the jaw members cooperate to grasp tissue therebetween. Each jaw member includes a jaw housing and an electrically conductive surface adapted to connect to a source of electrosurgical energy such that the electrically conductive surfaces are capable of conducting electrosurgical energy through tissue held therebetween to effect a tissue seal. A cutting mechanism with a sharpened leading edge is fixed between the jaw members near a proximal end thereof. The sharpened leading edge of the cutting mechanism is positioned to cut tissue between the jaw members upon forward movement of the jaw members along the tissue seal. A stop member may be disposed at the distal end of one of the jaw members that is dimensioned to maintain a gap distance between the jaw members during electrical activation of the electrically conductive surfaces.

In one embodiment, the stop member is operatively affixed to a guide rail-system disposed within one of the jaw housings that allows the jaw members and the cutting mechanism to move forward over the stop member to sever tissue along the tissue seal.

The present disclosure also relates to an end effector assembly for use with an instrument for sealing and cutting tissue and includes a pair of opposing first and second jaw members movable relative to the other from a first position wherein the jaw members are disposed in spaced relation relative to one another to a second position wherein the jaw members cooperate to grasp tissue therebetween. Each jaw member includes a jaw housing and an electrically conductive surface adapted to connect to a source of electrosurgical energy such that the electrically conductive surfaces are capable of conducting electrosurgical energy through tissue held therebetween to effect a tissue seal. One or both of the jaw members includes an elongated perforation strip that extends inwardly from the electrically conductive surface thereof. The elongated perforation strip is dimensioned to perforate the tissue upon closure of the jaw members against tissue and activation of the electrically conductive surfaces to effect a tissue seal. The perforation strips on each respective jaw member may be configured to intermesh with one another upon closure of the jaw members against tissue and activation of the electrically conductive surfaces to effect a tissue seal.

BRIEF DESCRIPTION OF THE DRAWINGS

Various embodiments of the subject instrument are described herein with reference to the drawings wherein.

DETAILED DESCRIPTION

Figure 1A:
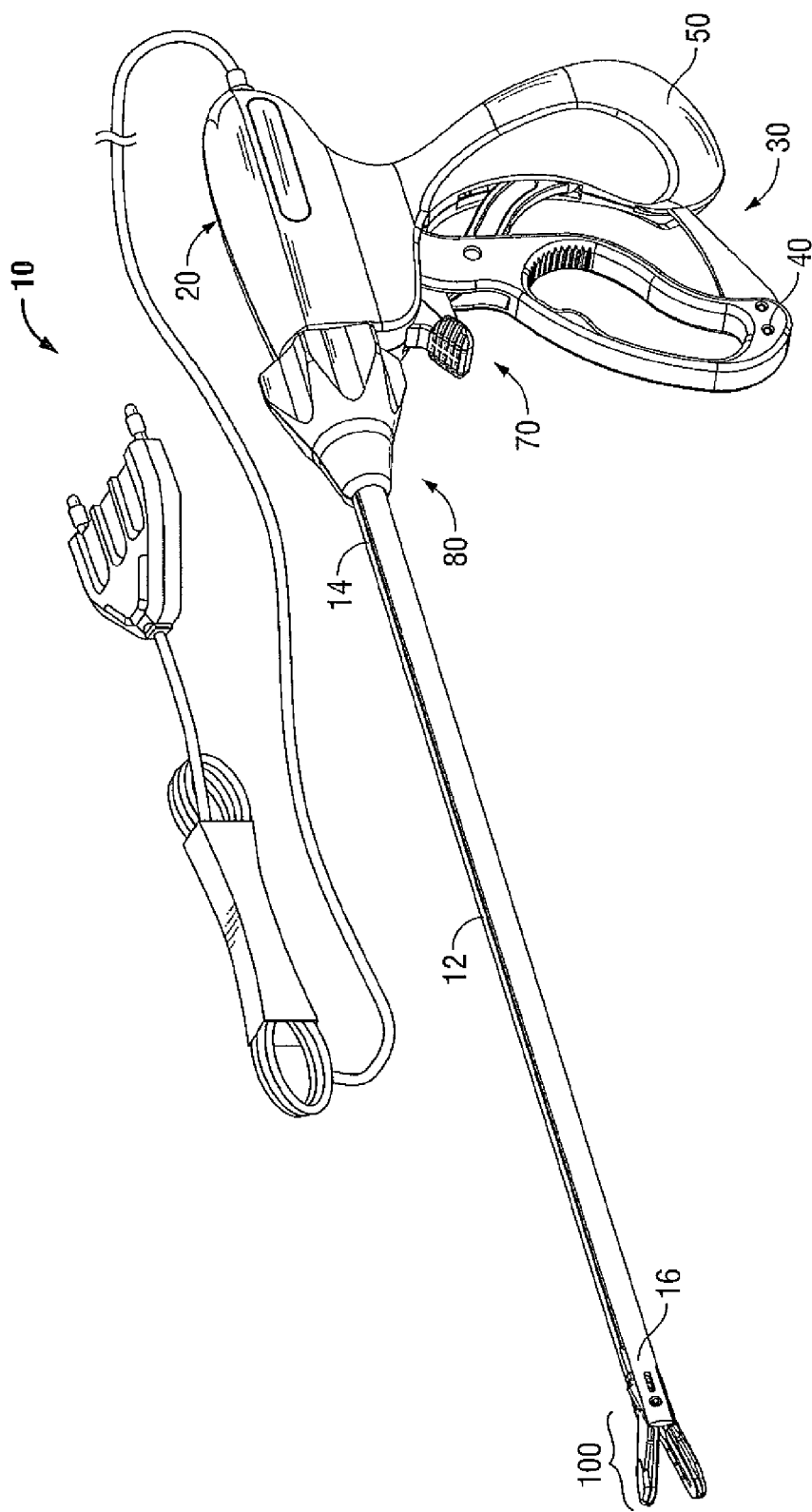
FIG. 1A is a right, perspective view of an prior art endoscopic bipolar forceps having a housing, a shaft and an end effector assembly having a pair of opposing jaw members affixed to a distal end thereof.
Figure 1B:
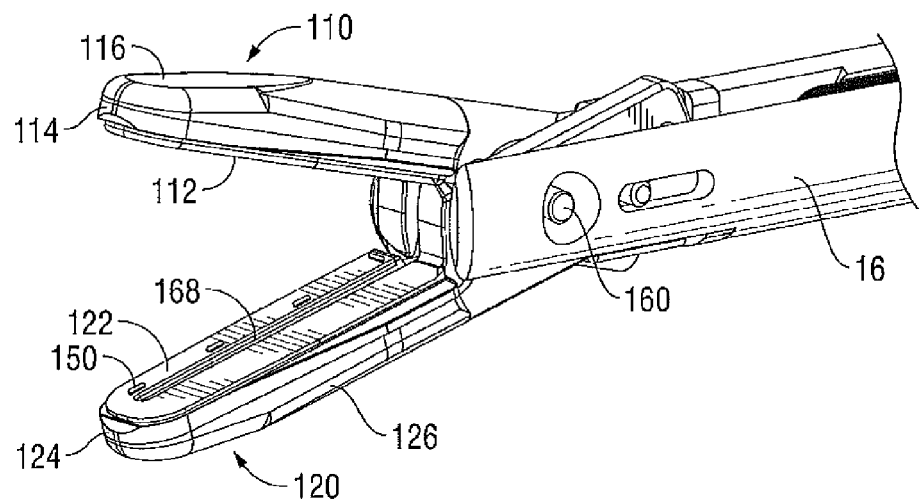
FIG. 1B is an enlarged, left perspective view of the end effector assembly with the jaw members shown in an open configuration.
Figure 1C:
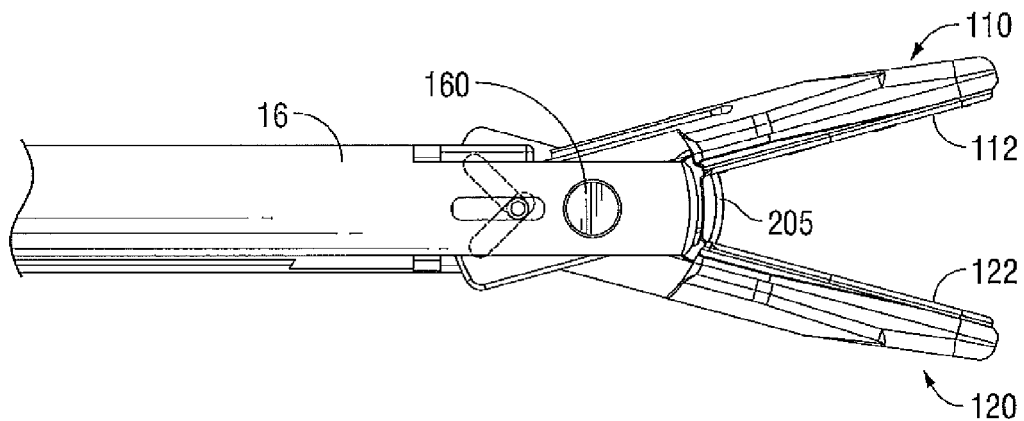
FIG. 1C is an enlarged, right side view of the end effector assembly of FIG. 1B.

Referring initially to FIGS. 1A-1C, a bipolar forceps for use in connection with endoscopic surgical procedures is depicted. For the purposes herein, either an endoscopic instrument or an open instrument may be utilized with the various electrode assemblies described herein. Obviously, different electrical and mechanical connections and considerations apply to each particular type of instrument, however, the novel aspects with respect to the electrode assembly and the operating characteristics associated therewith remain generally consistent with respect to both the open or endoscopic designs.

Generally, the end effector designs depicted herein are used to cut tissue along a vessel seal. However, any one of the various designs may be utilized to cut tissue after electrically treating tissue in a different fashion (e.g., coagulating or cauterizing tissue) or for simply cutting tissue without necessarily electrically treating tissue.

Bipolar forceps 10 generally includes a housing 20, a handle assembly 30, a rotating assembly 80, a switch assembly 70 and an electrode assembly 105 having opposing jaw members 110 and 120 that mutually cooperate to grasp, seal and divide tubular vessels and vascular tissue. More particularly, forceps 10 includes a shaft 12 that has a distal end 16 dimensioned to mechanically engage the electrode assembly 100 and a proximal end 14 that mechanically engages the housing 20. The shaft 12 may include one or more known mechanically engaging components that are designed to securely receive and engage the electrode assembly 100 such that the jaw members 110 and 120 are pivotable relative to one another to engage and grasp tissue therebetween.

The proximal end 14 of shaft 12 mechanically engages the rotating assembly 80 to facilitate rotation of the electrode assembly 100. In the drawings and in the descriptions which follow, the term "proximal", as is traditional, will refer to the end of the forceps 10 which is closer to the user, while the term "distal" will refer to the end which is further from the user. Details relating to the mechanically cooperating components of the shaft 12 and the rotating assembly 80 are described in commonly-owned U.S. patent application Ser. No. 11/827,297 entitled "VESSEL SEALER AND DIVIDER".

Handle assembly 30 includes a fixed handle 50 and a movable handle 40. Fixed handle 50 is integrally associated with housing 20 and handle 40 is movable relative to fixed handle 50 to actuate the opposing jaw members 110 and 120 of the electrode assembly 100 as explained in more detail below.

As mentioned above, electrode assembly 100 is attached to the distal end 16 of shaft 12 and includes the opposing jaw members 110 and 120. Movable handle 40 of handle assembly 30 imparts movement of the jaw members 110 and 120 about a pivot 160 from an open position wherein the jaw members 110 and 120 are disposed in spaced relation relative to one another, to a clamping or closed position wherein the jaw members 110 and 120 cooperate to grasp tissue therebetween.

Referring now to FIGS. 1B and 1C, enlarged views of an end effector assembly 100 of a prior device are shown in an open position for approximating tissue. Jaw members 110 and 120 are generally symmetrical and include similar component features which cooperate to permit facile rotation about pivot pin 160 to effect the sealing and dividing of tissue. As a result and unless otherwise noted, only jaw member 110 and the operative features associated therewith are describe in detail herein but as can be appreciated, many of these features apply to jaw member 120 as well.

Jaw member 110 also includes a jaw housing 116, an insulative substrate or insulator 114 and an electrically conducive surface 112. Insulator 114 is configured to securely engage the electrically conductive sealing surface 112. This may be accomplished by stamping, by overmolding, by overmolding a stamped electrically conductive sealing plate and/or by overmolding a metal injection molded seal plate. All of these manufacturing techniques produce an electrode having an electrically conductive surface 112 that is substantially surrounded by an insulating substrate 114.

As mentioned above, jaw member 120 includes similar elements which include: a jaw housing 126; insulator 124; and an electrically conducive sealing surface 122 that is dimensioned to securely engage the insulator 124. Electrically conductive surface 122 and the insulator 124, when assembled, form a longitudinally-oriented channel 168 defined therethrough for reciprocation of the knife blade 205. Knife channel 168 facilitates longitudinal reciprocation of the knife blade 205 along a preferred cutting plane to effectively and accurately separate the tissue along the formed tissue seal. Although not shown, jaw member 110 may also include a knife channel that cooperates with knife channel 168 to facilitate translation of the knife through tissue.

Jaw members 110 and 120 are electrically isolated from one another such that electrosurgical energy can be effectively transferred through the tissue to form a tissue seal. Electrically conductive sealing surfaces 112 and 122 are also insolated from the remaining operative components of the end effector assembly 100 and shaft 12. A plurality of stop members 150 may be employed to regulate the gap distance between the sealing surfaces 112 and 122 to insure accurate, consistent and reliable tissue seals.

FIGS. 2-7 show various embodiments of different jaw member configurations for selectively cutting tissue disposed between opposing jaw members. Although is some instances only one jaw member, e.g., jaw member 220, 320 and 420 is shown for the various envisioned embodiments, it should be understood that a complementary jaw member having similar operating components may be utilized for sealing purposes or to facilitate the cutting process.

Figure 2:
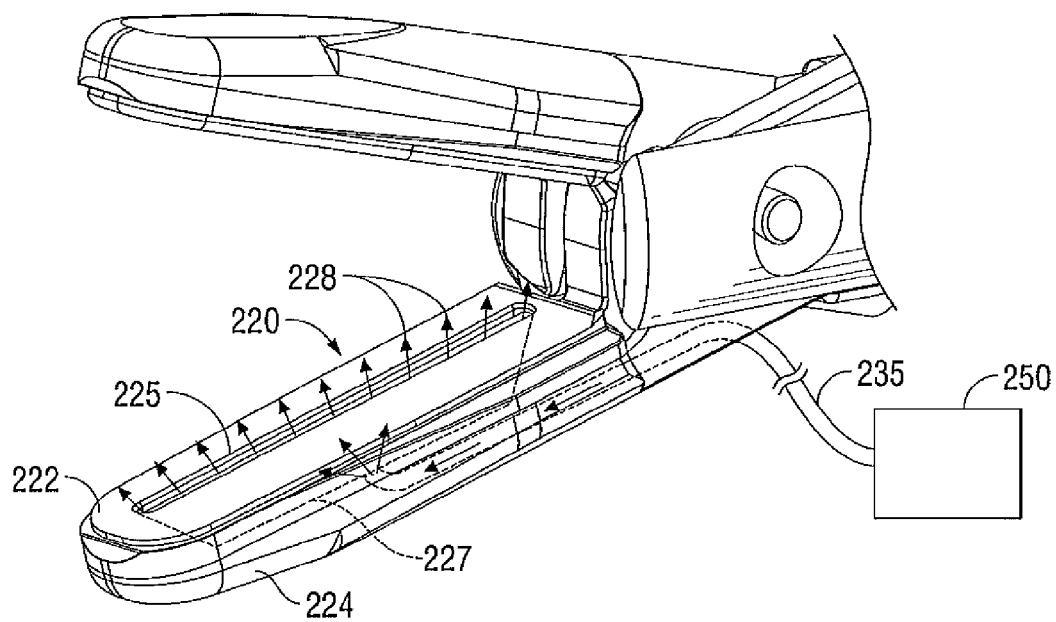
FIG. 2 is an enlarged, left perspective view of an alternate embodiment of an end effector assembly according to the present disclosure having a high pressure fluid nozzle disposed therein for cutting tissue.

FIG. 2 shows one embodiment of a jaw member 220 for use with the forceps 10 described above. Jaw member 220 includes an insulative housing 224 having an electrically conductive surface 222 disposed thereon configured for conducting energy to tissue. A longitudinally-oriented channel 225 is defined within the electrically conductive surface 222 and extends from a proximal end of the conductive surface 222 to a distal end thereof. Channel 225 is configured to fluidly communicate with a nozzle 227 disposed in housing 224, which is, in turn, operatively coupled to a high pressure fluid supply 250 via conduit 235 disposed through jaw member 220. Nozzle 227 is configured to redirect the flow of fluid 228 from the high pressure fluid supply 250 and conduit 235 into the channel 225. Nozzle 227 may be geometrically configured, e.g., longitudinally and/or transversally tapered, to increase the fluid pressure and/or mold or shape the fluid 228 exiting the nozzle 227 and channel 225 into a knife-like stream for cutting tissue disposed between the jaw members.

Jaw member 220 cooperates with an opposing jaw member (not shown) to approximate and seal tissue disposed therebetween. The opposing jaw member may be configured in a similar manner to direct a knife-like stream of fluid 228 into tissue to cut the tissue from an opposing direction to facilitate the cutting process. Configuring both jaw members in this manner may facilitate the cutting process and enhance the overall cutting effect. The opposing fluid channel (not shown) may be connected to the same or an independent fluid source (via a second conduit (not shown)) depending upon a particular purpose.

In use, the user initially energizes the opposing electrically conductive surface 222 and, for example, sealing plate 112 of FIG. 1, to effectively seal tissue disposed between the jaw members as described above. Once the tissue is sealed or otherwise treated, a visual or audible warning is typically displayed or otherwise transmitted to the user to indicate completion of the treatment process. If desired, the user then initiates the cutting process to separate the tissue along the tissue seal (or treatment area) by opening one or more valves 255 to induce the high pressure fluid 228 through the conduit 235 to the nozzle 227. The high pressure fluid 228 is directed into tissue 225 to effectively sever the tissue along the longitudinally-oriented channel in the sealing surface 222.

As mentioned above, the opposing jaw member (not shown) may include a similar configuration to enhance the cutting effect by directing high pressure fluid 228 into tissue from the opposite direction. Alternatively, the tissue may be cut without initially sealing or otherwise treating tissue.

Figure 3A:
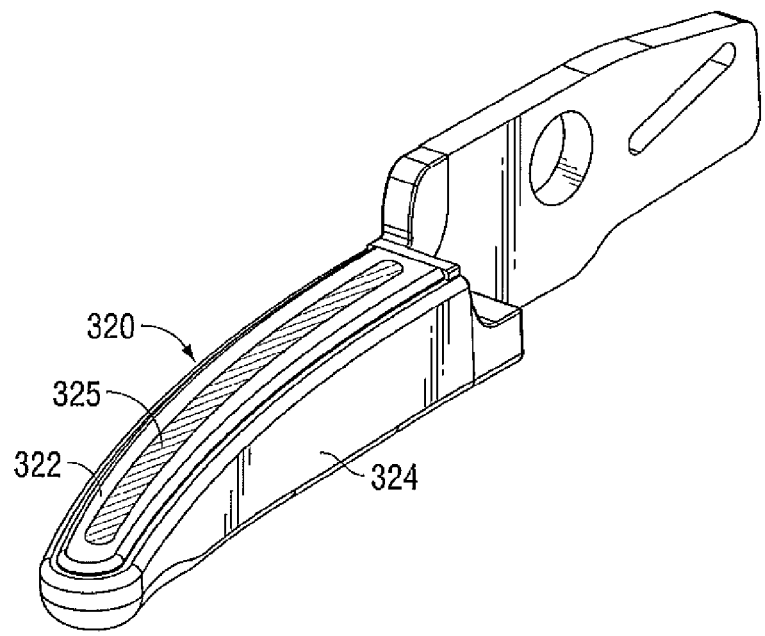
FIG. 3A is an enlarged, left perspective view of an alternate embodiment of an end effector assembly according to the present disclosure having a centrally disposed adhesive strip for cutting tissue.

FIG. 3A shows another embodiment of a jaw member 320 for use with the forceps 10 described above. Jaw member 320 includes an insulative housing 324 having an electrically conductive surface 322 disposed thereon configured for conducting energy to tissue. Similar to the embodiment of the jaw member described in FIG. 2 above, jaw member 320 cooperates with an opposing jaw member (not shown) to approximate and seal tissue disposed therebetween. The opposing jaw member may be configured in a similar manner to tear tissue from an opposing direction to facilitate the cutting process.

Jaw member 320 is configured to include a longitudinally-oriented strip of adhesive 325 disposed along sealing surface 322. Adhesive strip 325 is configured to both facilitate retention of tissue during the initial treatment of tissue (e.g., tissue sealing) and effectively grip the tissue along the center of the tissue seal to induce the tissue to tear therealong when the jaw members 320 (opposing jaw member not shown) are removed. The adhesive strip 325 may be a heat-activated adhesive or a heat-enhanced adhesive to facilitate the tearing, i.e., cutting, process.

Figure 3B:
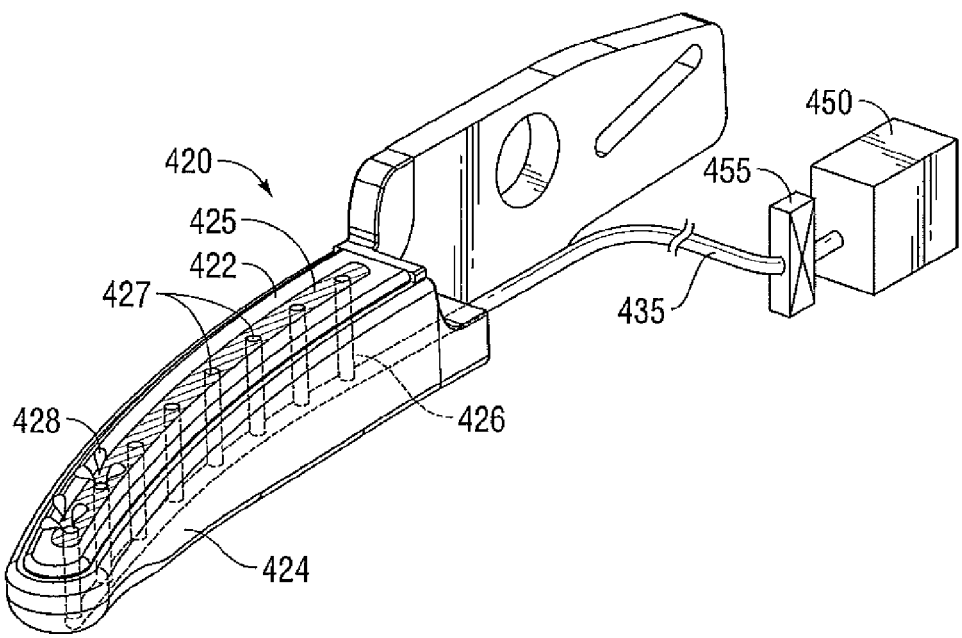
FIG. 3B is an enlarged, left, perspective view of an alternate embodiment of an end effector assembly according to the present disclosure having a centrally disposed adhesive strip for cutting tissue that is operably coupled to an adhesive fluid supply.

FIG. 3B shows a similar embodiment of a jaw member 420 for use with the forceps 10 which also utilizes an adhesive 428 to effective tear tissue along a tissue seal. Jaw member 420 includes an insulative housing 424 having an electrically conductive surface 422 disposed thereon configured for conducting energy to tissue. Similar to the embodiments above, jaw member 420 cooperates with an opposing jaw member (not shown) to approximate and seal tissue disposed therebetween. The opposing jaw member may be configured in a similar manner to tear tissue from an opposing direction to facilitate the cutting process.

A longitudinally-oriented strip 425 is defined within the electrically conductive surface 422 and extends from a proximal end of the conductive surface 422 to a distal end thereof. Strip 425 is configured to include a plurality of nozzles 426 disposed in housing 424, which are, in turn, operatively coupled to a fluid adhesive supply 450 via conduit 435 disposed through jaw member 420. Nozzles 426 are configured to direct the flow of adhesive fluid 428 from the supply 450 and conduit 435 onto strip 425 through corresponding nozzle ports 427 arranged longitudinally along strip 425. Nozzle ports 427 may be geometrically configured, e.g., longitudinally and/or transversally tapered, to direct the flow of the adhesive 428 fluid onto the strip in a uniform and consistent manner to facilitate separation of tissue.

Adhesive 428 is configured to both facilitate retention of tissue during the initial treatment of tissue (e.g., tissue sealing) and effectively grip the tissue along the center of the tissue seal to induce the tissue to tear therealong when the jaw members 420 (opposing jaw member not shown) are removed. The adhesive 428 may be a heat-activated adhesive or a heat-enhanced adhesive to facilitate the tearing, i.e., cutting, process. Moreover, the adhesive may be simultaneously or sequentially administered during or after the creation of a tissue seal. For example, the surgeon may initially energize the jaw members to seal tissue disposed therebetween and then open a valve to administer the adhesive 428 along the strip 425. The adhesive 428 then cures and grips the tissue to promote separation thereof when the jaw members are removed. The conduit 435 may also be fluidly connected to a cleaning fluid supply (not shown) which dissolves the adhesive 428 on the strip 425 between uses such that the remaining tissue may be washed away after separation from the tissue seal.

Figure 4A:
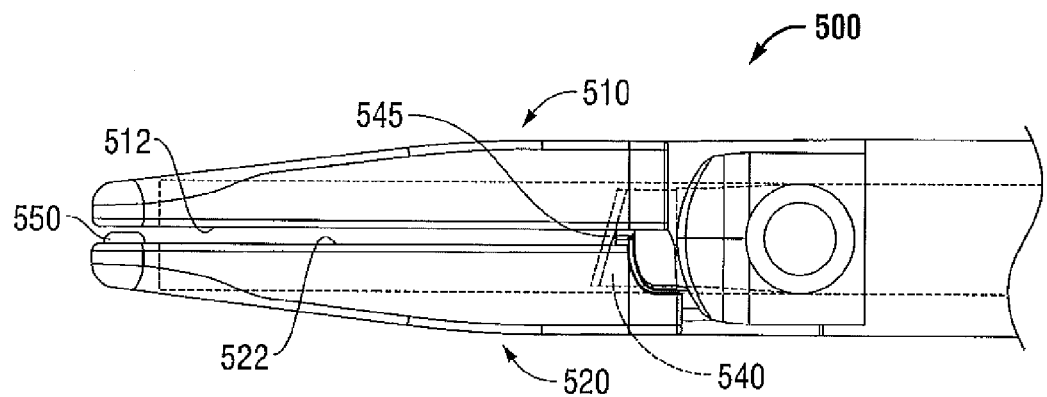
FIG. 4A is an enlarged, side view of an alternate embodiment of an end effector assembly according to the present disclosure having a centrally disposed fixed cutter.

FIG. 4A shows yet another embodiment of a cutting mechanism for forceps 10 and includes end effector assembly 500 having opposing jaw members 510 and 520 that are moveable relative to one another to engage tissue therebetween to effect a tissue seal. Jaw members 510 and 520 include respective jaw housings 516 and 524 that support electrically conductive surface 512 and 522, respectively. Each electrically conductive surface 512 and 522 is adapted to connect to an electrical energy source such that the electrically conductive surfaces 512 and 522 may conduct energy to tissue disposed therebetween to effectively treat, e.g., seal, tissue upon activation of the electrosurgical generator (not shown).

A cutting mechanism 540 is fixed between the jaw members 510 and 520 near a proximal end thereof. The cutting mechanism 540 includes a sharpened edge 545 at a distal end thereof. Once the tissue is treated, e.g., sealed, the surgeon relaxes the closing pressure of the jaw members 510 and 520 against the tissue (e.g., by relaxing the jaw handle 40 (See FIG. 1)) and simply moves the jaw members 510 and 520 forward such that the sharpened edge 545 of the knife 540 severs tissue along the tissue seal. A stop member 550 may be disposed at the distal end of one of the jaw members, e.g., jaw member 520, to maintain a gap distance between the jaw members 510 and 520 during electrical activation to effectively seal tissue.

Figure 4B:
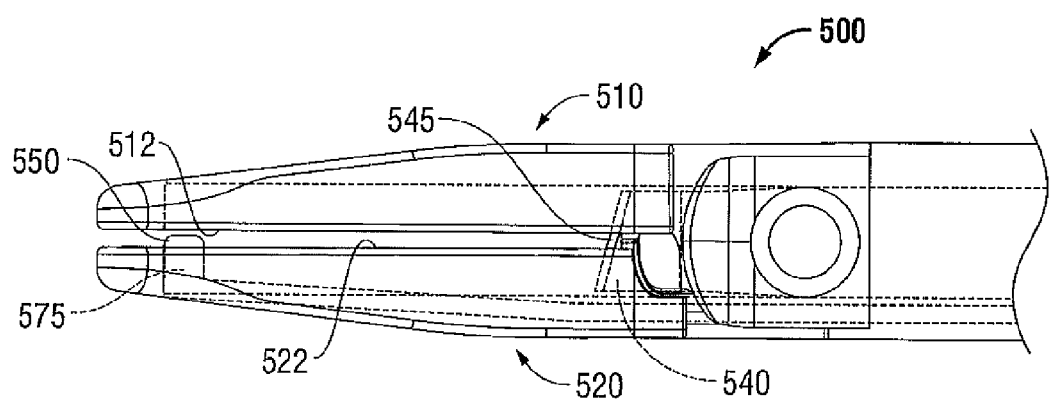
FIG. 4B is an enlarged, side view of an alternate embodiment of an end effector assembly according to the present disclosure having a centrally disposed fixed cutter that is configured to ride atop an isolated stop member, the jaw members and the cutter being shown in a first retracted position before tissue cutting.
Figure 4C:
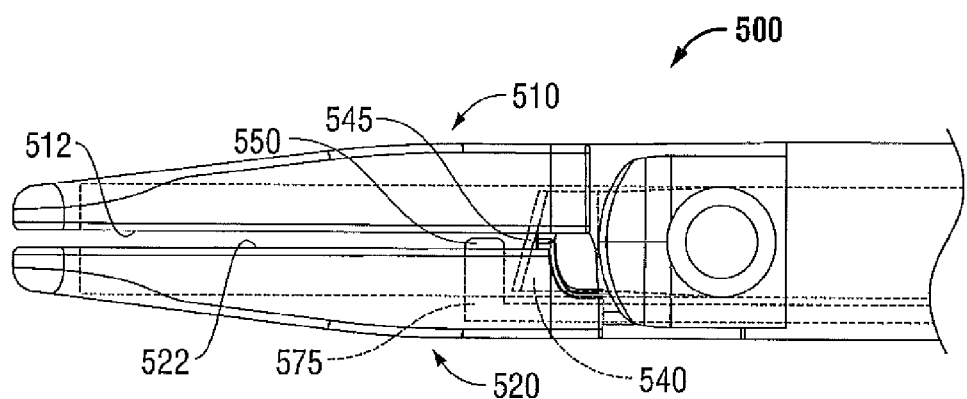
FIG. 4C is an enlarged, side view of an alternate embodiment of an end effector assembly according to the present disclosure having a centrally disposed fixed cutter that is configured to ride atop an isolated stop member, the jaw members and the cutter being shown in a second extended position after tissue cutting.

Alternatively and as shown in FIGS. 4B and 4C, the stop member 550 may operatively couple to a guide rail-system 575 that allows the jaw members 510 and 520 and the knife 540 to move forward over the fixed stop member 550 to sever tissue along the tissue seal. The knife 540 remains fixed relative to the jaw members 510 and 520 during distal movement of the jaw members 510 and 520 over the stop member 550 (see FIG. 4C).

Figure 5:
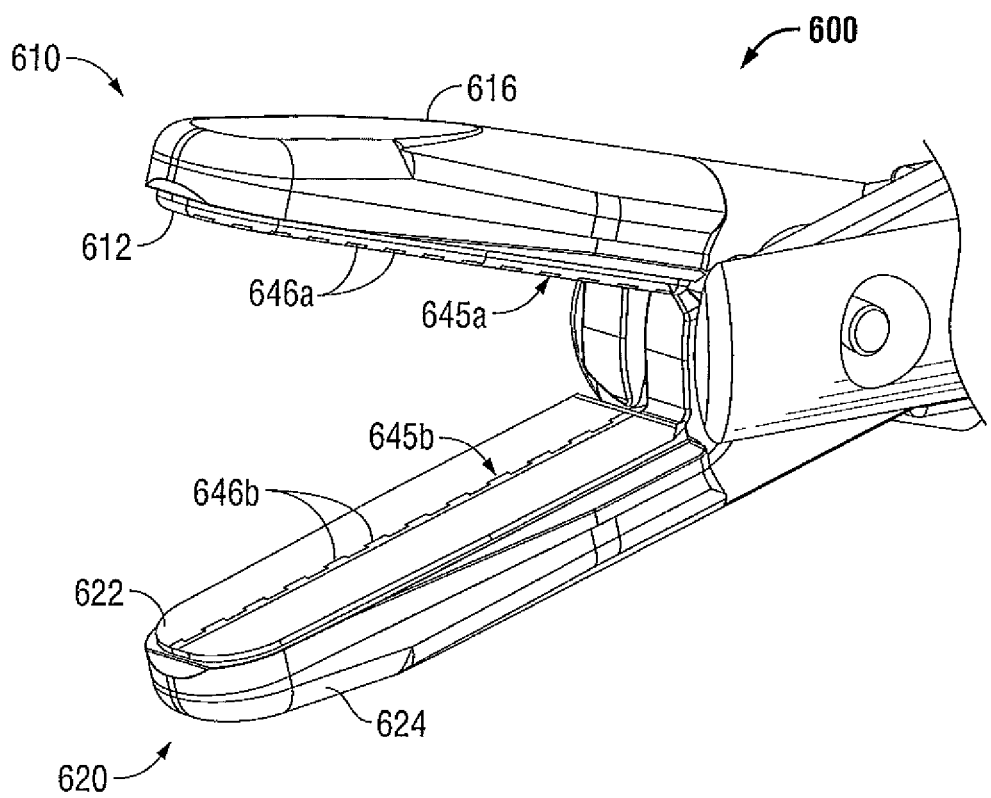
FIG. 5 is an enlarged, right perspective view of an alternate embodiment of an end effector assembly according to the present disclosure having a pair of opposing centrally disposed perforating strips dimensioned to perforate tissue upon closure of the jaw members against tissue.

FIG. 5 shows yet another embodiment of a cutting mechanism for forceps 10 and includes end effector assembly 600 having opposing jaw members 610 and 620 that are moveable relative to one another to engage tissue therebetween to effect a tissue seal. Jaw members 610 and 620 include respective jaw housings 616 and 624 that support electrically conductive surfaces 612 and 622, respectively, that are each adapted to connect to an electrical energy source to conduct energy to tissue disposed between the jaw members to effectively seal tissue.

Each jaw member 610 and 620 includes an elongated perforation strip 645a and 645b, respectively, that extends inwardly from each respective electrically conductive surface 612 and 622. The perforation strip 645a and 645b are aligned in general vertical registration relative to one another and each strip 645a and 645b includes a series of teeth 646a and 646b, respectively, that are configured to intermesh with one another upon closure of the jaw members 610 and 620. Alternatively, only one jaw member, e.g., jaw member 620, may be configured to include the perforating strip 645b.

In use, tissue is grasped between jaw members 610 and 620 and closed under a predetermined working pressure to effectively treat tissue, e.g., under a working pressure of about 3 $kg/cm^2$ to about 16 $kg/cm^2$ to seal tissue. The perforating strips 645a and 645b act to both grip the tissue for manipulation purposes and perforate the tissue along the center of the electrically conductive surface 612 and 622. After electrosurgical activation of the electrically conductive surfaces 612 and 622, the jaw members 610 and 622 are released revealing a perforated tissue line centrally-disposed between the conductive surfaces 612 and 622. The surgeon thereafter tears the perforated tissue along the perforation to separate the two tissue halves.

The perforation strips 645a and 645b may be insulative or electrically conductive depending upon a particular purpose or may be made from a reactive material which heats up during electrical activation to facilitate the perforation process.

From the foregoing and with reference to the various figure drawings, those skilled in the art will appreciate that certain modifications can also be made to the present disclosure without departing from the scope of the present disclosure. For example, it is contemplated that cutting mechanism may be dimensioned as a cutting wire or cutting blade that is selectively activatable by the surgeon to divide the tissue after sealing. More particularly, a wire or cutting blade is mounted within the insulator between the jaw members and is selectively energizable upon activation of a separate switch or simultaneously with the activation of the sealing switch.

Although the specification and drawings disclose that the electrically conductive surfaces may be employed to initially seal tissue prior to cutting tissue in one of the many ways described herein, it is also envisioned that the electrically conductive surfaces may be configured and electrically designed to perform any known bipolar or monopolar function such as electrocautery, hemostasis, and/or desiccation utilizing one or both jaw members to treat the tissue. Moreover, the jaw members in their presently described and illustrated formation may be energized or positioned to simply cut tissue without initially treating tissue which may prove beneficial during particular surgical procedures.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. An end-effector assembly for use with an electrosurgical instrument, the end-effector assembly comprising:
   opposing jaw members, at least one of the jaw members movable relative to the other from a first position wherein the jaw members are disposed in spaced relation relative to one another to at least a second position closer to one another wherein the jaw members cooperate to grasp tissue therebetween;
   at least one of the jaw members including an electrically-conductive surface adapted to connect to a source of electrosurgical energy such that the electrically-conductive surface is capable of conducting electrosurgical energy through tissue held between the jaw members and an electrical return to effect a tissue seal; and
   the at least one jaw member including an elongated perforation strip that extends inwardly from the electrically-conductive surface thereof, the elongated perforation strip configured to perforate tissue upon closure of the jaw members against tissue and activation of electrosurgical energy.

2. The end-effector assembly of claim 1, wherein the elongated perforation strip is formed of an electrically-conductive material.

3. The end-effector assembly of claim 1, wherein the elongated perforation strip is formed of an insulative material.

4. The end-effector assembly of claim 1, wherein the elongated perforation strip is formed of a reactive material configured to generate heat during activation of the electrically-conductive surface to facilitate perforation of tissue.

5. The end-effector assembly of claim 1, wherein each of the jaw members includes an electrically-conductive surface and an elongated perforation strip that extends inwardly from the electrically-conductive surface thereof.

6. An end-effector assembly for use with an electrosurgical instrument, the end-effector assembly comprising:
   opposing jaw members, at least one of the jaw members movable relative to the other from a first position wherein the jaw members are disposed in spaced relation relative to one another to at least a second position closer to one another wherein the jaw members cooperate to grasp tissue therebetween;
   an electrically-conductive surface disposed on each of the jaw members in spaced apart opposing registration relative to one another, each electrically-conductive surface adapted to connect to a source of electrosurgical energy such that the electrically conductive surfaces are capable of conducting electrosurgical energy through tissue held therebetween to effect a tissue seal; and
   elongated perforation strip disposed on each of the jaw members that extends inwardly from respective electrically-conductive surfaces, the elongated perforation strips on each respective jaw member configured to intermesh with one another upon closure of the jaw members against tissue and activation of the electrically conductive surfaces to effect a tissue seal.

7. The end-effector assembly of claim 6, wherein the elongated perforation strip of at least one of the jaw members is formed of an electrically-conductive material.

8. The end-effector assembly of claim 6, wherein the elongated perforation strip of at least one of the jaw members is formed of an insulative material.

9. The end-effector assembly of claim 6, wherein the elongated perforation strip of at least one of the jaw members is formed of a reactive material configured to generate heat during activation of the electrically-conductive surfaces to facilitate perforation of tissue.

10. The end-effector assembly of claim 6, wherein the elongated perforation strip of each of the jaw members is configured to perforate tissue along a center line of the electrically conductive surface thereof.

11. A method of treating tissue, comprising:
    providing an electrosurgical instrument having an end-effector assembly including opposing jaw members, at least one of the jaw members including an elongated perforation strip that extends inwardly from an electrically-conductive surface thereof;
    positioning the jaw members in a first configuration wherein the jaw members cooperate to grasp tissue therebetween;
    transmitting energy from an electrosurgical power generating source to at least one of the jaw members to activate the electrically-conductive surface thereof;
    positioning the jaw members in a second configuration wherein the jaw members are disposed in spaced relation relative to one another; and
    separating tissue along a perforated tissue line, where the perforated tissue line is formed by the elongated perforation strip when the jaw members are disposed in the first configuration.

12. The method of treating tissue of claim 11, wherein the providing includes at least one of the jaw members including an elongated perforation strip formed of a reactive material configured to generate heat during activation of the electrically-conductive surfaces to facilitate perforation of tissue.

* * * * *